(12) United States Patent
Spaulding et al.

(10) Patent No.: US 8,197,125 B2
(45) Date of Patent: Jun. 12, 2012

(54) ENHANCED PHOTOPROTECTIVE COMPOSITIONS AND METHODS FOR THE EVALUATION THEREOF

(75) Inventors: Laura A. Spaulding, Wayne, NJ (US); Alissa R. Frontauria, Lodi, NJ (US); Patricia L. Scott, Union, NJ (US)

(73) Assignee: Playtex Products, LLC, Shelton, CT (US)

( * ) Notice: Subject to any disclaimer, the term of this patent is extended or adjusted under 35 U.S.C. 154(b) by 546 days.

(21) Appl. No.: 12/359,009

(22) Filed: Jan. 23, 2009

(65) Prior Publication Data

US 2009/0196321 A1 Aug. 6, 2009

Related U.S. Application Data

(60) Provisional application No. 61/022,940, filed on Jan. 23, 2008.

(51) Int. Cl.
 *G01N 25/20* (2006.01)
 *G01N 22/00* (2006.01)
 *G01R 27/26* (2006.01)
(52) U.S. Cl. .............................. 374/45; 374/44; 374/122
(58) Field of Classification Search .................. 374/4, 5, 374/29, 43, 44, 45, 57, 122; 252/588, 589
 See application file for complete search history.

(56) References Cited

U.S. PATENT DOCUMENTS

| | | | | |
|---|---|---|---|---|
| 4,307,277 | A * | 12/1981 | Maeda et al. | 219/759 |
| 4,608,865 | A * | 9/1986 | Muller et al. | 73/204.23 |
| 5,191,183 | A * | 3/1993 | Balbaa et al. | 219/681 |
| 5,523,549 | A * | 6/1996 | Tenzer | 219/730 |
| 7,002,179 | B2 * | 2/2006 | Nakahara | 257/76 |
| 7,114,848 | B2 * | 10/2006 | Kaneko | 374/142 |
| 7,807,917 | B2 * | 10/2010 | Atanackovic | 136/236.1 |
| 2009/0185991 | A1 * | 7/2009 | Spaulding et al. | 424/59 |

FOREIGN PATENT DOCUMENTS

WO 9960994 12/1999

OTHER PUBLICATIONS

Birnboim, Amikam; et al "Modeling the Heat Wave Generated during Microwave Heating of Powdered Zinc Oxide in a Nitrogen Atmosphere"; Journal of the American Ceramic Society; vol. 82, No. 2, Feb. 1999; pp. 313-318.
Martin, L.P.; et al "Effects of Anomalous Permittivity on the Microwave Heating of Zinc Oxide"; Journal of Applied Physics, American Institute of Physics, New York; vol. 83, No. 1; Jan. 1998; pp. 432-437.
El-Idrissi, A.; et al "Mathematical Formulation of Microwave Heating for a Small Rod-Shaped Sample. Dielectric Study of Moistened Sands"; Modelling, Measurement & Control, vol. 7, No. 7-8, Jan. 2004; pp. 25-33.
Lorenz, Ralph D., "Rapid Communication Calorimetric Radar Absorptivity Measurement Using a Microwave Oven"; Meas. Sci. Technol.; vol. 10, No. 6, Great Britain, 1999; pp. L29-L32.
Nyfors, Ebbe; et al. "Industrial Microwave Sensors"; Artech House; Jan. 1989.
Heiland, H.; et al "Pyroelectricity of Zinc Oxide"; Solid State Communications; Great Britain; vol. 4, No. 7, Jul. 1966; pp. 353-356.
Kiess, Helmut "On the Decay of the Polarization Charge on Zinc Oxide Induced by the Pyroelectric Effect"; Solid State Communications; Great Britain; vol. 10, No. 12, Jun. 1972; p. 1107.
Lee, M.H.; et al "Pyroelectric Sensors"; Journal of Electroceramics; Kluwer Academic Publishers; vol. 2, No. 4; 1998; pp. 229-242.
International Search Report mailed on Feb. 10, 2010.

* cited by examiner

*Primary Examiner* — R. A. Smith
(74) *Attorney, Agent, or Firm* — Michaud-Kinney Group LLP

(57) ABSTRACT

A method of analyzing metal oxides. In this method, metal oxide is provided, heated with microwaves, and a conductivity parameter of the metal oxide is determined. From the conductivity parameter, a determination is made regarding a pyroelectric effect of the metal oxide.

11 Claims, 1 Drawing Sheet

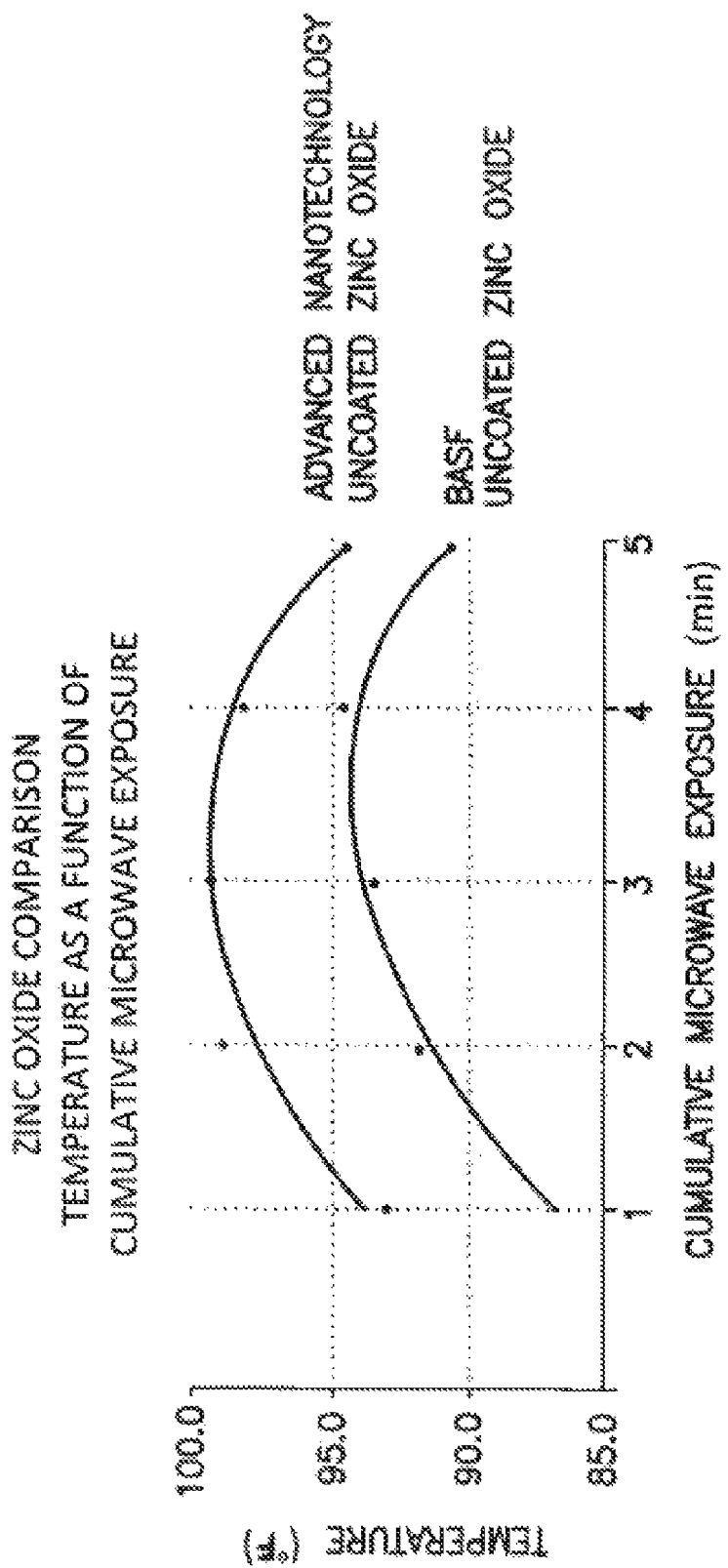

ENHANCED PHOTOPROTECTIVE COMPOSITIONS AND METHODS FOR THE EVALUATION THEREOF

CROSS REFERENCE TO RELATED APPLICATIONS

This application claims the benefits of U.S. Provisional Patent Application Ser. No. 61/022,940, filed Jan. 23, 2008, entitled "Enhanced Photoprotective Compositions," the content of which is incorporated herein by reference in its entirety.

TECHNICAL FIELD

The present invention is generally directed to photoprotective compositions and, more particularly, to photoprotective compositions in the form of topically applied sunscreens that provide protection from ultraviolet (UV) radiation and methods for evaluating the pyroelectric effects thereof.

BACKGROUND

The ability of a photoprotective composition to provide protection against UV radiation is typically expressed as the sun protection factor (SPF) of the composition. Photoprotective compositions having SPF values of 80 or more generally contain 15% homosalate, which is an acceptable amount of homosalate for compositions in the U.S. market. However, compositions in the international market are allowed to include only 10% homosalate. To maintain an SPF of 80 or more for the products available in the international market, it is therefore desirable to limit the homosalate thereof to 10%.

Zinc oxide has been indicated as being a material that is inherently pyroelectric. Pyroelectricity is the ability of a certain material to generate an electrical potential when the material is heated or cooled. As a result of this change in temperature, positive and negative charges migrate to opposite ends of the zinc oxide lattice structure (the material becomes polarized). Thus, an electrical potential is established.

Zinc oxide is also a semiconductor with a direct band gap energy ($E_g$) of 3.37 eV at room temperature. Most zinc oxide has n-type character (as opposed to p-type character, which is more difficult to attain), which means that electron energy levels near the top of the band gap allow an electron to be excited into the conduction band with relative ease. Native defects such as oxygen vacancies or zinc interstitials are often assumed to be the origin of this n-type character. Intentional doping of the n-type zinc oxide, which may be effected by introducing aluminum, indium, or excess zinc into the zinc oxide structure, allows the zinc oxide to be formed into thin films in which the zinc oxide serves as a transparent conducting oxide, which can be used to form a transparent electrode.

When a photon hits zinc oxide, one of three things can happen: (1) the photon can pass straight through the zinc oxide, which happens for lower energy photons; (2) the photon can reflect off the surface; or (3) the photon can be absorbed by the zinc oxide. If the photon is absorbed by the zinc oxide, either heat or electron-hole pairs may be generated. Electron-hole pairs are generated if the photon energy is higher than the zinc oxide band gap value.

An incident photon may be absorbed by the zinc oxide if its energy is greater than the semiconductor band gap energy. As a result, an electron from the valence band of the zinc oxide (wherein the electron comes from the oxygen) is promoted into the conduction band (the metal ion orbital). If the energy of the incident photon is less than the band gap energy, it will not be absorbed as this would require that the electron be promoted to within the band gap. This energy state is forbidden. Once promoted into the conduction band, however, the electron relaxes to the bottom of the conduction band with the excess energy emitted as heat to the crystal lattice.

When a photon is absorbed, its energy is given to an electron in the crystal lattice. Usually this electron is in the valence band and is tightly bound in covalent bonds between neighboring atoms, and hence unable to move far. The energy given to it by the photon "excites" the electron into the conduction band where it is free to move around within the semiconductor. The covalent bond that the electron was previously a part of now has one fewer electron (which results in the formation of a "hole"). The presence of a missing covalent bond allows the bonded electrons of neighboring atoms to move into the hole, thereby leaving another hole behind, and in this way a hole can "move" through the lattice. Thus, it can be said that photons absorbed in the semiconductor create mobile electron/hole pairs.

The holes act as positive particles in the valence band. Both the electrons and the holes are free to migrate around the zinc oxide particle. Electrons and holes may recombine emitting photons of energy equal to the band gap energy. However, the lifetime of an electron/hole pair is quite long due to the specific nature of the electronic band structure. Thus, there is sufficient time for an electron and a hole to migrate to the surface and react with absorbed species.

A photon need only have a greater energy than that of the band gap in order to excite an electron from the valence band into the conduction band. In the solar frequency spectrum, much of the radiation reaching the surface of the earth is composed of photons with energies greater than the band gap of silicon (1.12 eV) and zinc oxide (3.37 eV). The higher energy photons will be absorbed by the difference in energy between these photons, and the band gap energy is converted into heat via lattice vibrations (called phonons).

SUMMARY OF THE PRESENT INVENTION

In one aspect, the present invention resides in a method of analyzing metal oxides. In this method, metal oxide is provided, heated with microwaves, and a conductivity parameter of the metal oxide is determined. From the conductivity parameter, a determination is made regarding a pyroelectric effect of the metal oxide.

In another aspect, the present invention resides in a method of analyzing zinc oxide for a pyroelectric effect. This method includes the steps of providing zinc oxide, exposing at least the zinc oxide to microwave radiation, measuring a temperature increase of the zinc oxide, using this measured increase as an indicator of conductivity of the zinc oxide, and correlating the conductivity to a pyroelectric effect of the photoprotective composition.

In another aspect, the present invention resides in a method of evaluating a pyroelectric effect of zinc oxide. This method includes providing zinc oxide, heating the zinc oxide with microwaves, measuring a resistivity of the heated zinc oxide, and obtaining a value for the pyroelectric effect of the zinc oxide from the resistivity of the zinc oxide. The zinc oxide has an excess of zinc ions within an absorbing core, is n-doped, and includes micron-sized agglomerations of zinc oxide crystals.

BRIEF DESCRIPTION OF THE DRAWING

The FIGURE is a graphical representation of a comparison of temperature as a function of cumulative microwave exposure for zinc oxide.

DESCRIPTION OF THE PREFERRED EMBODIMENTS

All percentages of components are weight percentages. It should also be noted that while the present invention is exemplified below using zinc oxide, various metal oxide is within the scope of the invention.

The zinc oxide component of the present invention and for use in the dispersion of the present invention can have an average particle size of about 2.74 microns and still be transparent on the skin after application of a formulated product that includes this zinc oxide component. One zinc oxide that may be of particular use with regard to the present invention is a dispersion that includes 40-60% zinc oxide, 30-59% $C_{12-15}$ alkyl benzoate, and 1-5% isostearic acid (available as ZinClear-IM 50AB from Advanced Nanotechnology). The present invention is not limited to the use of $C_{12-15}$ alkyl benzoate, however, as other esters are within the scope of the present invention. Other zinc oxide components that may be used include, but are not limited to, 40-60% zinc oxide, 30-59% caprylic/capric triglyceride, and 1-5% glyceryl isostearate (available as ZinClear-IM 50CCT); uncoated zinc oxide and coated zinc oxide having an average particle size diameter of about 30-50 nanometers (available as Z-Cote from BASF); and coated zinc oxides in which coating is added (available as SIH-5 Z-Cote XP-M52 from BASF). The foregoing SIH-5 Z-Cote XP-M52 is a formulation of zinc oxide/silica/dimethicone methicone copolymer. Also of interest for use with zinc oxide or in addition to any of the foregoing zinc oxides is $C_{12-15}$ alkyl benzoate (available as FINSOLV TN) and caprylic/capric triglyceride (available as DERMOL M5). It should be understood that isostearic acid, triglycerides, and isostearates are derived from fatty acids.

Generally the zinc oxide lattice structure is "reduced." It is believed that in a zinc oxide in which the lattice structure is reduced, the zinc oxide particles possess an excess of zinc ions within an absorbing core. These are localized states and as such may exist within the band gap. However, the electrons and holes may then relax to the excess zinc ion states. Thus, the electrons and holes may be trapped so that they cannot migrate to the surface of the particles and react with absorbed species. The electrons and holes may then recombine at the ionic zinc states accompanied by the release of a photon with an energy equivalent to the difference in the energy levels.

Additionally, a crystal of the enhanced zinc oxide is smaller than the crystal size of other zinc oxides, thus giving the zinc oxide more surface area than other zinc oxides. Also, with regard to the zinc oxide of the present invention, smaller crystals are irreversibly aggregated so that the resulting particles have micron sizes instead of nanometer sizes before and after formulation.

The zinc oxide formed by the combination of the reduced zinc oxide crystals aggregated with the zinc oxide crystals of larger size may result in the formation of "trap sites" that affect conductivity of the zinc oxide material and therefore the pyroelectric effect. These trap sites, which minimize migration of the electron/hole pairs, may be luminescence trap sites and/or killer sites. Luminescence trap sites and killer sites are foreign ions designed to trap the electrons and positively charged holes and therefore inhibit migration of the electron/hole pairs.

Furthermore, the zinc oxides employed in the present invention are n-doped, thereby facilitating the movement of the electrons in one direction so they eventually cannot move anymore, and thereby resulting in a decrease in conductivity.

In methods of the present invention in which the pyroelectric effects of zinc oxide are evaluated, it is believed that if the photons of sunlight are absorbed by the zinc oxide, then the enhanced zinc oxide would be more effective at or capable of absorbing photons of light than non-enhanced zinc oxide. Because the pyroelectric effect is related to conductivity, it could be measured indirectly by subjecting the zinc oxide to microwaves. Increases in temperature could be used as indicators of pyroelectric effects. Higher temperatures indicate increased conductivity, and therefore increased pyroelectricity. This forms a basis to differentiate between zinc oxides and any changes influencing the crystal lattice structure.

The equipment used in the experiments below included an 1100 watt microwave. 120 volts oven (Model #NN-S7588A commercially available from Panosonic) and a digital thermometer (model # PT-100, Surface temperature Probe). The apparatus set-up for the temperature study is as follows. A weighed amount of powder or dispersion was placed in the bottom of a polycarbonate cup. The cup was set on an upside down styrene cup to avoid heat transfer from microwave floor. The sample was microwaved for a set period of time, and the temperature was immediately recorded. As the method became more refined, 1 gram of sample was microwaved on high for 1 minute, temperature measured immediately during one minute "rest" interval, and then microwaved again, etc. Procedure continued until temperature after microwaving was lower than previous reading. In these studies, the temperature probe was equilibrated to 83 C just prior to measurement of sample temperature to avoid heat loss when "warming up" the thermometer.

EXAMPLE 1

Comparison of Uncoated Zinc Oxide with Coated Zinc Oxide

In a first microwave study, 0.5 gram samples of zinc oxide were heated using microwaves for 60 seconds. The initial temperature for each sample was 75 degrees F. The highest temperature for the uncoated zinc oxide was 87.2 degrees F, and the highest temperature for the coated zinc oxide was 83.6 degrees F. It was determined that the coating on the coated zinc oxide interfered with the conductivity of the zinc oxide.

EXAMPLE 2

Comparison of Zinc Oxide and Alkyl Benzoate

Two gram samples of zinc oxide suspension (ZinClear-IM 50AB) and alkyl benzoate (FINSOLV TN) were heated using microwaves for 30 seconds. The initial temperature for each sample was 83 degrees F. The highest temperature for the ZinClear-IM 50AB was 105.5 degrees F. The highest temperature for the FINSOLV TN was 100.2 degrees F. It was determined that the ZinClear sample exhibited a pyroelectric effect, and that solvent for the dispersed zinc oxide also affects the pyroelectric effect.

EXAMPLE 3

Comparison of Zinc Oxide and Caprylic/Capric Triglyceride

Two gram samples of zinc oxide suspension (ZinClear-IM 50CCT) and caprylic/capric triglyceride (DERMOL M5)

were heated using microwaves for 30 seconds. The initial temperature for each sample was 83 degrees F. The highest temperature for the ZinClear-IM 50CCT was 99.4 degrees F. The highest temperature for the DERMOL M5 was 103.5 degrees F. It was determined that the ZinClear sample exhibited a pyroelectric effect, but that the 50CCT zinc oxide may be less pyroelectrically effective than the 50AB zinc oxide of Example 4. The waxy coating of isostearic acid versus glyceryl isostearate might also influence the pyroelectric effect of zinc oxide.

EXAMPLE 4

Comparison of Uncoated Zinc Oxides

In another microwave study, one gram of uncoated enhanced zinc oxide was placed in the bottom of a first polycarbonate cup, and one gram of uncoated non-enhanced zinc oxide was placed in the bottom of a second polycarbonate cup. The samples were subjected to intermittent heating by being heated using microwaves for one minute time periods with one minute rests in-between microwave exposures. Surface temperatures were recorded during the one minute rests. The temperature probe was warmed to 83 degrees F before contact with the sample surface. The testing was performed as routinely as possible to minimize data variability. Although some variability was noted, an overall general increase of about 5-6 Fahrenheit degrees was noted for the enhanced zinc oxide versus the non-enhanced zinc oxide.

The data showed a drop in temperature (conductance) after four one-minute exposures of high power microwaves, as shown in the FIGURE. The data shown in the FIGURE suggest that the electrons in the crystal lattice of the enhanced zinc oxide are easier to excite than the electrons in the crystal lattice of the non-enhanced zinc oxide.

It is postulated that the ease of excitation in the enhanced zinc oxide is due to the "reduction" in the zinc oxide lattice structure, that the size of the crystal in the enhanced zinc oxide is smaller and has more surface area than the crystal in the non-enhanced zinc oxide, and that the smaller crystals of the enhanced zinc oxide were irreversibly agglomerated so that the resulting particles are of micron sizes instead of nanometer sizes before and after formulation.

It is also postulated that a "reduced zinc oxide crystal" that has been "aggregated" gives rise to "trap sites" that affect conductivity and pyroelectric effect.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the following claims.

What is claimed is:

1. A method of analyzing a metal oxide, said method comprising the steps of:
   heating said metal oxide with cumulative microwave exposure;
   measuring a thermal response of said metal oxide to said microwave exposure;
   correlating said thermal response to a conductivity of said metal oxide; and
   correlating said conductivity to a pyroelectric effect of said metal oxide.

2. The method of claim 1, wherein said thermal response is a temperature.

3. The method of claim 1, wherein said step of heating said metal oxide comprises intermittent heating.

4. The method of claim 1, wherein said metal oxide is coated.

5. The method of claim 1, wherein said metal oxide is uncoated.

6. The method of claim 1, wherein said metal oxide is dispersed in a solvent.

7. A method of analyzing zinc oxide, said method comprising the steps of:
   heating said zinc oxide with cumulative microwave exposure;
   measuring a thermal response of said zinc oxide to said microwave exposure;
   correlating said thermal response to a conductivity of said zinc oxide; and
   correlating said conductivity to a pyroelectric effect of said zinc oxide.

8. The method of claim 7, wherein said zinc oxide is n-doped.

9. The method of claim 7, wherein said zinc oxide is selected from the group of coated zinc oxides and uncoated zinc oxides.

10. The method of claim 7, wherein said zinc oxide is dispersed in a solvent.

11. The method of claim 7, wherein said step of heating said zinc oxide with microwave exposure is intermittent heating.

\* \* \* \* \*